(12) United States Patent
Morgans, Jr. et al.

(10) Patent No.: US 6,537,996 B2
(45) Date of Patent: Mar. 25, 2003

(54) MODULATORS OF P38 MAP KINASE

(75) Inventors: David J. Morgans, Jr., Los Altos, CA (US); Silke Thode, Los Gatos, CA (US); Dongxu Sun, Cupertino, CA (US)

(73) Assignee: Iconix Pharmaceuticals, Inc., Mountain View, CA (US)

( * ) Notice: Subject to any disclaimer, the term of this patent is extended or adjusted under 35 U.S.C. 154(b) by 0 days.

(21) Appl. No.: 09/792,876

(22) Filed: Feb. 23, 2001

(65) Prior Publication Data

US 2001/0044440 A1 Nov. 22, 2001

Related U.S. Application Data

(60) Provisional application No. 60/184,368, filed on Feb. 23, 2000.

(51) Int. Cl.$^7$ ............... A61K 31/506; A61K 31/445; A61P 35/00; C07D 239/02; C07D 421/00
(52) U.S. Cl. ............... 514/256; 514/317; 514/318; 514/331; 544/242; 544/333; 544/334; 544/335; 546/192; 546/193; 546/194; 546/229
(58) Field of Search ............... 514/256, 317, 514/318, 331; 544/242, 333, 334, 335; 546/192, 193, 194, 229

(56) References Cited

FOREIGN PATENT DOCUMENTS

WO  WO 99/58502  11/1999

OTHER PUBLICATIONS

Buyuktimkin et al., "Auinazolines. XI: Modified Niementowski Reaction of Some Aromatic Amine," *J. Fac. Pharm.Istanbul* 21:53–62 Abstract XP001009715 (1985).
Gautier et al., "Preparation of Amidines From Aromatic Nitriles and Amines in Liquid Ammonia," *Bulletin De La Soc. Chimique De France* 1:200–207 XP002170423 (1970).
Hisano et al., "Synthesis and Antiinflammatory Activity of N1–(Substituted Pheny1) Pyridinecarboxamidines," *Chem. Pharm. Bull.* 314(7):2484–2490 Abstract XP002170421 (1983).
Hisano et al., "Synthesis of Benzoxazoles, Benzothiazoles and Benzimidazoles and Evaluation of Their Antifungal, Insecticidal and Herbicidal Activities," *Chem. Pharm. Bull.* 30(8):2996–3004 Abstract XP002170422 (1982).
Raynaud et al., "Anticonvulsant Properties of Diarylamidines," *Ann. Pharm. Fr.* 30(11):735–743 Abstract XP002170422 (1972).
Robba, M. Max, "Etude de l' Activité Antituberculeuse de Quelques Dérivés Nouveaux des Diazines," *Ann Pharm.* 18:23–25 Abstract XP 001009821(1960).
Robev et al., "Influence of Some Substituted Aromatic Amidines on Monoamine Oxidase Activity," *Dokl. Bulg. Akad. Nauk.* 44(1):67–69 Abstract XP001009723.

Primary Examiner—Richard L. Raymond
Assistant Examiner—Tamthom N. Truong
(74) Attorney, Agent, or Firm—Robins & Pasternak LLP

(57) ABSTRACT

Compounds of formula 1 are effective modulators of p38 MAP kinase.

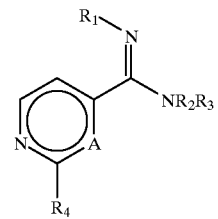

wherein $R_1$ is H, lower alkyl, or $OR_5$, where $R_5$ is aryl, heterocyclyl, acyl, N—$R_6$-4-piperidinyl, N—$R_6$-4-piperidinylmethyl, or N—$R_6$-4-pipelidinylethyl, where aryl and heterocyclyl are substituted with 1–3 $R_6$ substituents selected from the group consisting of H, lower alkyl, lower alkenyl, OH, $NO_2$, $NH_2$, halo, trihalomethyl, —CN, SH, SO, $SO_2$, $SO_3H$, —OR, —COR, —COOR, —CONHR, —OCOR, and —NCOR, where R is lower alkyl; $R_2$ is H or lower alkyl; $R_3$ is aryl substituted with 1–3 $R_6$ substituents; $R_4$ is H, lower alkyl, aryl, aralkyl, —OH, —$NH_2$, —NHR, or —OR, where R is lower alkyl or aryl-lower alkyl; and A is —CH— or —N—; and pharmaceutically acceptable salts thereof.

14 Claims, No Drawings

MODULATORS OF P38 MAP KINASE

CROSS-REFERENCE TO RELATED APPLICATION

This application is related to provisional patent application Ser. No. 60/184,368, filed Feb. 23, 2000, from which priority is claimed under 35 USC §119(e)(1) and which is incorporated herein by reference in its entirety.

FIELD OF THE INVENTION

This invention relates generally to the fields of molecular biology and pharmaceutical methods of treatment. More particularly, the invention relates to compounds, compositions, and methods for modulating p38 MAP kinase activity.

BACKGROUND OF THE INVENTION

Activation of members of the mitogen-activated protein kinase (MAPK) family represents one of the major mechanisms used by eukaryotic cells to transduce extracellular signals into cellular response (J. Blenis, *Proc Natl Acad Sci USA* (1993) 90:5889). One member of this kinase family, p38, has been implicated in signaling pathways used by biologically important stimuli including products of microbial pathogens, cytokines, UV light and increased extracellular osmolarity. Most recently p38 activation was found to be correlated with apoptosis in neuronal cells following withdrawal of nerve growth factor. The kinase p38 is activated by a subset of the known dual-specificity MAPK kinases (MEKs or MKKs); low molecular weight GTP-binding proteins RAC1 and Cdc42 have also been shown to play a role in regulating p38 activation by some stimuli. A complete understanding of how p38 activation regulates cellular responses requires identification of specific substrates for this enzyme.

SUMMARY OF THE INVENTION

We have now identified compounds that modulate the activity of p38.

One aspect of the invention is a compound of formula 1:

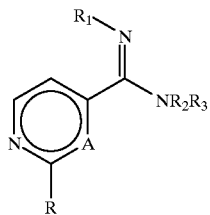

wherein $R_1$ is H, lower alkyl, or —$OR_5$, where $R_5$ is aryl, heterocyclyl, acyl, N—$R_6$-4-piperidinyl, N—$R_6$-4-piperidinylmethyl, or N—$R_6$-4-piperidinylethyl, where aryl and heterocyclyl are substituted with 1–3 $R_6$ substituents selected from the group consisting of H, lower alkyl, lower alkenyl, OH, $NO_2$, $NH_2$, halo, trihalomethyl, —CN, SH, SO, $SO_2$, $SO_3H$, —OR, —COR, —COOR, —CONHR, —OCOR, and —NCOR, where R is lower alkyl; $R_2$ is H or lower alkyl; $R_3$ is aryl substituted with 1–3 $R_6$ substituents as set forth above; $R_4$ is H, lower alkyl, aryl, aralkyl, —OH, —$NH_2$, —NHR, or —OR, where R is lower alkyl or aryl-lower alkyl; and A is —CH— or —N—; and pharmaceutically acceptable salts thereof.

Another aspect of the invention is a pharmaceutical composition, comprising a compound of formula 1 and a pharmaceutically acceptable excipient.

Another aspect of the invention is a method for modulating p38 activity in a cell, comprising administering an effective amount of a compound of formula 1 to said cell.

DETAILED DESCRIPTION

Definitions:

"Compound of formula 1" refers to compounds having the structure

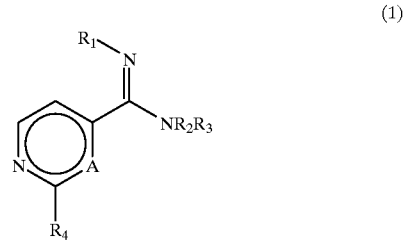

wherein $R_1$ is H, lower alkyl, or $OR_5$, where $R_5$ is aryl, heterocyclyl, acyl, N—$R_6$-4-piperidinyl, N—$R_6$-4-piperidinylmethyl, or N—$R_6$-4-piperidinylethyl, where aryl and heterocyclyl are substituted with 1–3 $R_6$ substituents selected from the group consisting of H, lower alkyl, lower alkenyl, OH, $NO_2$, $NH_2$, halo, trihalomethyl, —CN, SH, SO, $SO_2$, $SO_3H$, —OR, —COR, —COOR, —CONHR, —OCOR, and —NCOR, where R is lower alkyl; $R_2$ is H or lower alkyl; $R_3$ is aryl substituted with 1–3 $R_6$ substituents as set forth above; $R_4$ is H, lower alkyl, aryl, aralkyl, —OH, —$NH_2$, —NHR, or —OR, where R is lower alkyl or aryl-lower alkyl; and A is —CH— or —N—; and pharmaceutically acceptable salts and esters thereof. It should be noted that the two amidine nitrogen atoms can tautomerize if $R_2$ is H, in which case either $R_1$ or $R_3$ can be bound to the imide nitrogen (the nitrogen double-bonded to carbon). Thus, no absolute geometry is indicated or intended around the $R_1$—N=C bond.

The term "lower alkyl" refers to radicals containing carbon and hydrogen, without unsaturation, having from one to six carbon atoms, inclusive. Lower alkyl radicals can be straight or branched. Exemplary lower alkyl radicals include, without limitation, methyl, ethyl, propyl, isopropyl, hexyl, t-butyl, and the like. The term "lower alkenyl" refers to a hydrocarbon radical having 2–6 carbon atoms, and at least one double bond. Exemplary lower alkenyl radicals include, without limitation, vinyl, propenyl, butenyl, and the like.

The term "aryl" refers to an aromatic carbocyclic or heterocyclic moiety, having one, two, or three rings. Exemplary aryl radicals include, without limitation, phenyl, naphthyl, pyridyl, pyrimidyl, triazyl, quinazolinyl, pyranyl, thiazolyl, and the like. The terms "aralkyl" and "aryl-lower alkyl" refer to an aryl moiety joined to a lower alkyl moiety, for example benzyl, phenethyl, 2-phenylpropyl, naphthylmethyl, and the like.

The term "halo" refers to fluoro, chloro, bromo, and iodo.

The term "leaving group" refers to a radical that is easily displaced by a nucleophile in an $S_N2$ displacement reaction. Exemplary leaving groups include, without limitation, sulfonates such as tosylate and mesylate, silanes such as t-butyl-dimethylsilane, halogens such as bromo and chloro, and the like.

The term "pharmaceutically acceptable salts and esters" refers to derivatives of compounds of formula 1 obtained by addition of an acid or base to the compound, or condensation with an alcohol or carboxylic acid to form an ester. In either case, the acid, base, alcohol, or carboxylic acid must not be unacceptably toxic at the concentrations at which the compound is administered. Suitable acids include, without limitation, inorganic acids such as hydrochloric acid, hydrobromic acid, sulfuric acid, nitric acid or phosphoric acid; organic acids such as acetic acid, propionic acid, glycolic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid and the like.

The term "modulate" as used herein refers to an alteration in p38 MAP kinase activity, and includes both increases and decreases in activity. Modulation of activity can occur as the result of direct interaction of a compound with p38, interaction with another compound or protein that affects p38 activity directly or indirectly, or by altering the expression of p38 or of a protein that interacts with p38 directly or indirectly.

General Method:

Compounds of the invention are prepared by any suitable synthetic scheme. For example, an intermediate of formula A can be treated with an alcohol (R—OH) and NaH or Na—OR to form intermediate B.

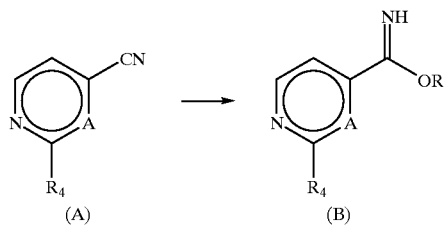

Intermediate B can then be treated with an intermediate of the form $R_1$—L (where L is a leaving group) in the presence of a strong, hindered base to provide an intermediate of formula C. This intermediate is then treated with an amine of the formula $HNR_2R_3$ under acidic or basic catalysis to provide the compound of formula 1.

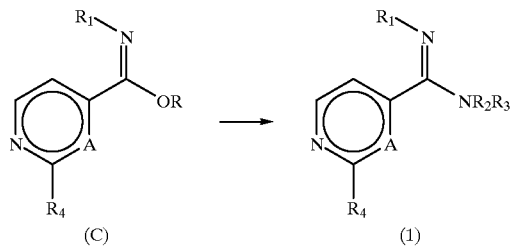

Compounds of the invention can be tested for activity by any available assay suitable for determining p38 activity or interference therewith.

Compounds of the invention can be administered to a subject, or can be applied directly to cells, for example in a cell culture. If administered to a cell culture, the compound is preferably first suspended or dissolved in a suitable carrier. Suitable carriers include, without limitation, water, saline solution, dimethylsulfoxide (DMSO) and solutions thereof, cell culture media, and the like.

Useful pharmaceutical carriers for the preparation of the pharmaceutical compositions hereof can be solids or liquids. Thus, the compositions can take the form of tablets, pills, capsules, powders, sustained release formulations, solutions, suspensions, elixirs, aerosols, and the like. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Other suitable pharmaceutical carriers and their formulations are described in "Remington's Pharmaceutical Sciences" by E. W. Martin.

A compound of formula 1 or a pharmaceutical composition containing same is administered via any of the usual and acceptable methods known in the art, either singly or in combination with another compound or compounds of the present invention or other pharmaceutical agents. These compounds or compositions can thus be administered orally, systemically (e.g., transdermally, intranasally or by suppository) or parenterally (e.g., intramuscularly, subcutaneously and intravenously), and can be administered either in the form of solid or liquid dosages including tablets, solutions, suspensions, aerosols, and the like, as discussed in more detail above. It is preferred to administer compounds of formula 1 orally. The formulation can be administered in a single unit dosage form for continuous treatment or in a single unit dosage form ad libitum when relief of symptoms is specifically required.

EXAMPLES

The following examples are provided as a guide for the practitioner of ordinary skill in the art. Nothing in the examples is intended to limit the claimed invention. Unless otherwise specified, all reagents are used in accordance with the manufacturer's recommendations, and all reactions are performed at ambient temperature and pressure.

Example 1

(p38 Assay)

(A) Protocol: Recombinant p38 was pre-incubated for 30 minutes at room temperature in ADB (Assay Dilution Buffer: 20 mM MOPS, pH 7.2, 20 mM $MgCl_2$, 5 mM EGTA, 1 mM DTT, 25 mM β-glycerolphosphate, 2 mM pNPP, 0.1 mM sodium orthovanadate) with recombinant GST-ATF-2 and compounds at various concentrations. The DMSO concentration was held constant at 0.1% (v/v) independent of the compound concentration. Kinase reactions were started with a mixture of $^{32}$P-γ-ATP and ATP in ADB and were incubated for 30 minutes at 37° C. Final concentrations in kinase reactions was 0.625 ng/μl recombinant p38 (Biomol, catalog number SE-150), 62.5 ng/μl recombinant GST-ATF-2 (Upstate Biotechnology, catalog #12-367) and 30 μM ATP (Amersham, catalog #AA0068, used within two weeks of the reference date). Reactions were terminated by the addition of stopmix (final concentrations: 62.5 mM Tris pH 6.8, 10% (v/v) glycerol, 5% (v/v) B-mercaptoethanol, 20 mg/ml SDS, 1 mg/ml bromophenol blue). At this point samples were either processed directly or stored at 4° C. For analysis, samples were heated to 95° C. for 5 min and proteins were separated by SDS-PAGE using 8–16% precast gels (Novex). Following electrophoresis, gels were stained in 0.25% (w/v) brilliant blue R, 40% (v/v) methanol and 7% (v/v) acetic acid to visualize protein bands. Gels were then incubated with 2% glycerol and exposed overnight to PhosphoImager screens (Molecular Dynamics). Screens were scanned using a PhosphoImager SI (Molecular Dynamics) and the amount of radioactive $^{32}$P incorporated into GST-ATF-2 was quantified using ImageQuant (Molecular Dynamics) software. Data were normalized against control samples treated with DMSO and were plotted as percent of p38 activity of samples as compared to control. $IC_{50}$ values were estimated by estimating from the graph the concentration of each compound at which p38 activity reached 50% of the control.

(B) Results: In the above-described assay, two tested compounds (X and Y below) demonstrated activity.

X

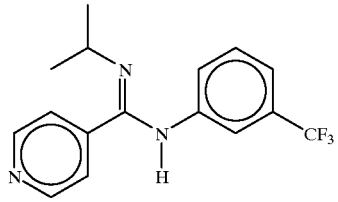

Y

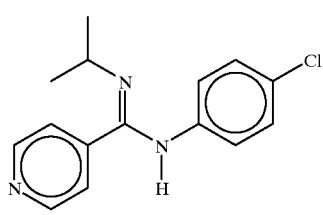

N-(3-trifluoromethylphenyl)-N'-isopropyl-4-amidinopyridine (X) exhibited an $IC_{50}$ of 0.75 μM, while N-(4-chloromethylphenyl)-N'-isopropyl-4-amidinopyridine (Y) exhibited an $IC_{50}$ of 4.0 μM. In growth rescue ARC experiments performed in yeast (following the methods taught in U.S. Ser. No. 09/187,918, WO/99/24563, both incorporated herein by reference in full), the compounds demonstrated an in vivo $IC_{50}$ of 13.2 μM and 546.2 μM, respectively.

What is claimed:

1. A compound of formula 1:

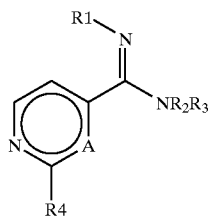

wherein $R_1$ is lower alkyl, or $OR_5$, where $R_5$ is aryl, heterocyclyl, acyl,

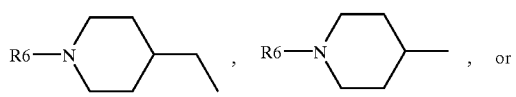

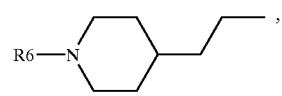

where
aryl and heterocyclyl are substituted with 1–3 $R_6$ substituents selected from the group consisting of H, lower alkyl, lower alkenyl, OH, $NO_2$, $NH_2$, halo, trihalomethyl, —CN, SH, SO, $SO_2$, $SO_3H$, —OR, —COR, —COOR, —CONHR, —OCOR, and —NCOR, where R is lower alkyl;

$R_2$ is H or lower alkyl;
$R_3$ is aryl substituted with 1–3 $R_6$ substituents;
$R_4$ is H, lower alkyl, aryl, aralkyl, —OH, —$NH_2$, —NHR, or —OR, where R is lower alkyl or aryl-lower alkyl; and
A is —CH— or —N—;
and pharmaceutically acceptable salts thereof.

2. The compound of claim 1, wherein $R_4$ is H and A is —CH—.

3. The compound of claim 2, wherein $R_1$ is lower alkyl and $R_2$ is H.

4. The compound of claim 3, wherein $R_3$ is —($C_6H_2$)$R_9R_8R_7$, wherein $R_9$, $R_8$, and $R_7$ are each independently H, lower alkyl, lower alkyl substituted with one or more halo, lower alkenyl, OH, $NO_2$, $NH_2$, halo, trihalomethyl, —CN, SH, SO, $SO_2$, $SO_3H$, —OR, —COR, —COOR, —CONHR, —OCOR, and —NCOR, where R is lower alkyl.

5. The compound of claim 4, wherein $R_1$ is isopropyl, $R_9$ is 3-trifluoromethyl, and $R_8$ and $R_7$ are each H.

6. The compound of claim 1, wherein A is —N— and $R_4$ is —NHR.

7. A method for modulating p38 activity, comprising: administering to a subject cell that expresses p38 an effective amount of a compound of formula 1:

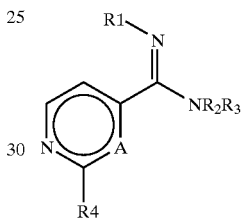

wherein $R_1$ is H, lower alkyl, or $OR_5$, where $R_5$ is aryl, heterocyclyl, acyl,

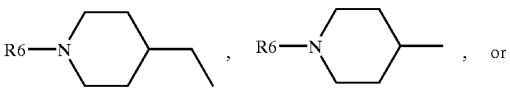

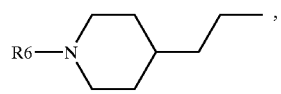

where
aryl and heterocyclyl are substituted with 1–3 $R_6$ substituents selected from the group consisting of H, lower alkyl, lower alkenyl, OH, $NO_2$, $NH_2$, halo, trihalomethyl, —CN, SH, SO, $SO_2$, $SO_3H$, —OR, —COR, —COOR, —CONHR, —OCOR, and —NCOR, where R is lower alkyl;

$R_2$ is H or lower alkyl;
$R_3$ is aryl substituted with 1–3 $R_6$ substituents;
$R_4$ is H, lower alkyl, aryl, aralkyl, —OH, —$NH_2$, —NHR, or —OR, where R is lower alkyl or aryl-lower alkyl; and
A is —CH— or —N—;
and pharmaceutically acceptable salts thereof.

8. The method of claim 7, wherein said subject cell comprises a mammalian cell in a cell culture.

9. The method of claim 7, wherein said subject cell comprises a cell within an organism.

10. A pharmaceutical composition, comprising:
a compound of formula 1,

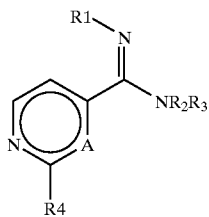

wherein $R_1$ is lower alkyl, or $OR_5$, where $R_5$ is aryl, heterocyclyl, acyl,

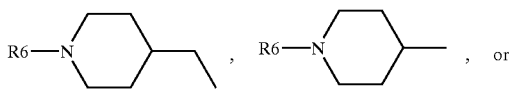

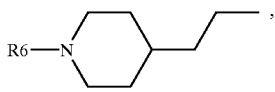

where aryl and heterocyclyl are substituted with 1–3 $R_6$ substituents selected from the group consisting of H, lower alkyl, lower alkenyl, OH, $NO_2$, $NH_2$, halo, trihalomethyl, —CN, SH, SO, $SO_2$, $SO_3H$, —OR, —COR, —COOR, —CONHR, —OCOR, and —NCOR, where R is lower alkyl;

$R_2$ is H or lower alkyl;

$R_3$ is aryl substituted with 1–3 $R_6$ substituents;

$R_4$ is H, lower alkyl, aryl, aralkyl, —OH, —$NH_2$, —NHR, or —OR, where R is lower alkyl or aryl-lower alkyl; and A is —CH— or —N—; and pharmaceutically acceptable salts thereof; and a pharmaceutically acceptable carrier.

11. The composition of claim 10, wherein $R_4$ is H and A is —CH—.

12. The compound of claim 11, wherein $R_1$ is lower alkyl and $R_2$ is H.

13. The compound of claim 12, wherein $R_3$ is —($C_6H_2$)$R_9R_8R_7$, wherein $R_9$, $R_8$, and $R_7$ are each independently H, lower alkyl, lower alkyl substituted with one or more halo, lower alkenyl, OH, $NO_2$, $NH_2$, halo, SH, SO, $SO_2$, $SO_3H$, —OR, —COR, —COOR, —CONHR, —OCOR, and —NCOR, where R is lower alkyl.

14. The compound of claim 13, wherein $R_1$ is isopropyl, $R_9$ is 3-trifluoromethyl, and $R_7$ and $R_8$ are each H.

* * * * *